US00PP26797P2

(12) United States Plant Patent
Bradford et al.

(10) Patent No.: US PP26,797 P2
(45) Date of Patent: Jun. 7, 2016

(54) NECTARINE TREE NAMED 'PEARLICIOUS X'

(50) Latin Name: *Prunus persica*
Varietal Denomination: Pearlicious X

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 38 days.

(21) Appl. No.: 14/544,244

(22) Filed: Dec. 15, 2014

(51) Int. Cl.
*A01H 5/08* (2006.01)

(52) U.S. Cl.
USPC ..... Plt./188

(58) Field of Classification Search
USPC ..... Plt./188
CPC ..... A01H 5/0856; A01H 5/0837
See application file for complete search history.

(56) References Cited

U.S. PATENT DOCUMENTS

PP12,570 P2 4/2002 Bradford
PP18,778 P2 4/2008 Bradford

*Primary Examiner* — Kent L Bell

(57) ABSTRACT

The present invention relates to a new and distinct variety of nectarine tree, *Prunus persica*, broadly characterized by a medium size, vigorous, hardy, self-fertile, productive and regular bearing tree. The variety blooms somewhat early and requires about 450 chilling hours. The fruit matures under the ecological conditions described in July, with first picking on Jul. 12, 2014. The fruit is medium to large in size, a tasty balance of acid and sugar in flavor, globose in shape, clingstone in type, very firm and crisp in texture, yellowish white in flesh color, and deep red in skin color.

1 Drawing Sheet

Botanical classification: *Prunus persica.*
Variety denomination: 'PEARLICIOUS X'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits, usually to capture recessive traits. The present invention relates to a new and distinct variety of nectarine tree, which has been denominated varietally as 'Pearlicious X'.

The present variety was hybridized by us in 2002 as a first generation cross using 'Snow Princess' (U.S. Plant Pat. No. 12,570) peach as the selected seed parent and an unnamed nectarine as the selected pollen parent. The fruit of this cross was gathered that summer, and the seeds were removed from the fruit, germinated, cracked, stratified, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2007 we selected the present variety as a single tree from the group of seedlings described above. Subsequent to origination of the present variety of nectarine tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'Snow Princess' (U.S. Plant Pat. No. 12,570) peach, by blooming in the early season, by being self-fertile, and by producing fruit that is globose in shape, mostly red in skin color, and yellowish white in flesh color, but is distinguished therefrom by having globose instead of reniform leaf glands and by producing fruit that is nectarine instead of peach, that is clingstone instead of freestone, and that matures six days earlier.

The present variety is most similar to 'Majestic Pearl' (U.S. Plant Pat. No. 18,778) nectarine by being a vigorous tree, by being self-fertile, and by producing nectarines that are clingstone in type, globose in shape, full red in skin color, genetically white in flesh color, and firm in texture, but is distinguished therefrom by blooming earlier, by requiring less chilling hours, by having globose instead of reniform leaf glands, and by producing fruit that is somewhat sweeter and slightly more acidic in flavor, and that matures eight days later.

SUMMARY OF VARIETY

In summary, the present nectarine variety is characterized by a medium size, vigorous, hardy, self-fertile, productive and regular bearing tree. The variety blooms somewhat early and requires about 450 chilling hours. The fruit matures under the ecological conditions described in July, with first picking on Jul. 12, 2014. The fruit is medium to large in size, a tasty balance of acid and sugar in flavor, globose in shape, clingstone in type, very firm and crisp in texture, yellowish white in flesh color, and deep red in skin color.

DRAWING

The accompanying photograph consists of four whole fruits positioned to display the characteristics of the skin color and form, one divided fruit to reveal the flesh and stone, two insets to reveal buds and a blossom, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 17, 2014, on a multiplied tree using 'Nemaguard' (unpatented) rootstock during its sixth growing season. The blossom and flower descriptions were made the previous blooming season. All major color code designations are by reference to the Inter-Society Color Council, National Bureau of Standards. Common color names are also used occasionally.

It is to be noted that 2014 was an abnormal year with drought conditions existing in California. The unusually clear, warm, and dry weather in January led to a very low amount of acquired chilling units, an earlier than normal blooming season, and an earlier than normal ripening season for the entire spring and summer.

PARENTAGE

Seed parent: 'Snow Princess' (U.S. Plant Pat. No. 12,570).
Pollen parent: Unnamed nectarine (unpatented).

TREE

Size: Medium, reaching and maintaining a height of 10' [3.05 m.] and a spread of 7' [2.13 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright.

Form: Vase formed.

Hardiness: Hardy with respect to central California winters.

Approximate chilling requirement: 450 hours.

Heat tolerance: Observed to perform adequately in typical central California climatic conditions, which typically include extended periods of heat.

Drought tolerance: Variety is developed for commercial orchards and requires regular irrigation.

Production: Productive.

Fertility: Self-fertile.

Bearing: Regular bearer with no alternate bearing yet observed.

Trunk:

- *Size*.—Medium, reaching a maximum diameter of 4½" [114.3 mm.] after twelve growing seasons.
- *Texture*.—Medium, shaggy.
- *Bark color*.—A Grayish reddish brown [46. gy.rBr] and Grayish brown [61. gy.Br] variegation.
- *Lenticels*.—Approximate Number Per Square Inch: 14. Color: Brownish orange [54. brO]. Average Size: 5/16" [7.9 mm.] in length and 3/32" [2.4 mm.] in width. Shape: Eye-shaped, elongated.

Branches:

- *Size*.—Diameter of limb is 2½" [63.5 mm.] measured 12" above the crotch, 1¼" [31.8 mm.] measured 12" above the first fork.
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. Second Year and Older Wood: Strong yellowish brown [74. s.yBr].
- *Lenticels*.—Number Per Square Inch: About 120 on second year wood. Color: Brownish orange [54. brO]. Average size: Small, 1/16" [1.6 mm.] in length and 1/64" [0.4 mm.] in width on second year wood. Shape: Elongated.

Leaves:

- *Size*.—Medium. Average Length: 5¼" [133.4 mm.]. Average Width: 1⅞" [47.6 mm.].
- *Arrangement*.—Alternate.
- *Thickness*.—Medium.
- *Form*.—Elliptical.
- *Apex*.—Acuminate.
- *Base*.—Acute with an average angle of 75 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: 7/16" [11.1 mm.]. Average Thickness: 1/16" [1.6 mm.]. Color: Brilliant yellow green [116. brill.YG].
- *Stipules*.—Number: Usually 2 per leaf, up to 6 per growing tip. Average Length: ¼" [6.4 mm.]. Color: Brilliant yellow green [116. brill.YG] becoming Dark yellowish brown [78. d.yBr] with maturity.
- *Glands*.—Number: Mostly 2 per leaf. Position: Mostly alternate, a few opposite. Size: Small, 1/48" [0.5 mm.] in diameter. Form: Globose. Color: Strong yellow green [117. s.YG] acquiring a Dark brown [59. d.Br] center with age. Location: At the intersection of petiole and base of blade.
- *Leaf buds*.—Pointed, medium in size.

Flower buds:

- *Hardiness*.—Hardy, with respect to central California winters.
- *Diameter*.—Typically ⅜" [9.5 mm.] 1 week before bloom.
- *Length*.—Typically 9/16" [14.3 mm.] 1 week before bloom.
- *Form*.—Not appressed.
- *Surface*.—Pubescent.
- *Tip color*.—Light purplish pink [249. l.pPk].

Flowers: Perfect, complete, perigynous, usually a single pistil, about thirty stamens, five sepal and petal locations alternately positioned.

- *Type*.—Showy, large.
- *Average flower diameter*.—2" [50.8 mm.].
- *Average flower depth*.—½" [12.7 mm.] when fully open.
- *Number of petals*.—Always five full petals with about fifty percent have extra petals or petal fragments, full double blossoms occur on about one percent.
- *Petal shape*.—Circular to oval.
- *Petal margin*.—Entire, slightly wavy with a few notches.
- *Average petal diameter*.—11/16" [17.5 mm.].
- *Average petal length*.—¾" [19.1 mm.].
- *Petal apex*.—Rounded.

*Petal base*.—Rounded.
*Petal color*.—Pale pink [7. p.Pk] toward the apex, Deep purplish pink [248. deep pPk] toward the base on both sides.
*Anther color*.—Deep red [13. deep R] over a Light yellow [86. l.Y] center at bloom onset.
*Pollen*.—Anthers produce an abundance of Brilliant yellow [83. brill.Y] pollen.
*Stigma color*.—Pale greenish yellow [104. p.gY].
*Stigma position*.—Typically located about 1/16" [1.6 mm.] above the nearby anthers.
*Ovary*.—Non-pubescent.
*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—1/4" [6.4 mm.].
*Sepal width*.—3/16" [4.8 mm.].
*Sepal apex*.—Rounded to elliptical to match the sepal length and width.
*Sepal margin*.—Fairly smooth.
*Average pistil length*.—3/4" [19.1 mm.].
*Average stamen length*.—9/16" [14.3 mm.].
*Fragrance*.—Moderate.
*Blooming period*.—Early to medium, blooms about four days before 'Majestic Pearl' (U.S. Plant Pat. No. 18,778) nectarine.
*Onset of bloom*.—One percent on Feb. 12, 2014.
*Date of full bloom*.—Feb. 20, 2014.
*Duration of bloom*.—One to two weeks, dependent on ambient temperature.
*Number per cluster*.—1 to 3 with single flowers most common.

FRUIT

Maturity when described: Firm ripe, Jul. 17, 2014.
Date of first picking: Jul. 12, 2014.
Date of last picking: Jul. 22, 2014.
Size: Variable, medium to large.
*Average diameter axially*.—2 7/8" [73 mm.].
*Average diameter across suture plane*.—3 1/16" [77.8 mm.].
*Average diameter across cheek plane*.—3" [76.2 mm.].
*Typical weight*.—8.5 ounces [241 grams].
Form: Uniform, globose, somewhat compressed axially, symmetrical.
*Longitudinal section form*.—Somewhat oblate.
*Axial view*.—Round with a hump at the suture.
Suture: Extends from the base, continues along the side, and ends just past the pistil point.
*Near the base*.—A sharp groove.
*Along the side*.—A shallow groove.
*Near the apex*.—A deep groove with marked depressions on both sides of the pistil point.
Ventral surface: Rounded, lipped stronger toward the apex on both sides.
Lips: Equal near the apex, somewhat unequal along the sides.
Cavity: Flaring, elongated in the suture plane, suture showing on one side, Light yellowish pink [28. l.yPk] stem markings present.
*Depth*.—3/4" [19.1 mm.].
*Breadth*.—1 1/4" [31.8 mm.].
Base: Truncate.
Apex: Rounded to slightly truncate, but strongly cordate if viewed parallel to the suture.
Pistil point: Apical, negligible in length, depressed within the suture.
Stem: Medium.
*Average length*.—3/8" [9.5 mm.].
*Average width*.—3/16" [4.8 mm.].
Skin:
*Thickness*.—Medium.
*Surface*.—Smooth.
*Tenacity*.—Tenacious to flesh.
*Astringency*.—Non-astringent.
*Tendency to crack*.—None observed.
*Color*.—Very deep red [17. v.d.R] over a background of Deep red [13. deep R] with a moderate amount of Light orange yellow [70. l.OY] freckling stronger toward the apex.
Flesh:
*Color*.—Yellowish white [92. yWhite] with Moderate red [15. m.R] streaking toward the stone.
*Surface of pit cavity*.—Very deep red [14. v.deep R] broken fibers when twisted from stone.
*Amygdalin*.—Slight.
*Juice*.—Abundant, rich.
*Texture*.—Very firm, crisp, melting.
*Fibers*.—Abundant, fine.
*Ripens*.—Fairly even.
*Flavor*.—A tasty balance of acid and sugar, very sweet, typically 18 to 22 Brix.
*Aroma*.—Very slight.
*Eating quality*.—Excellent.

STONE

Type: Clingstone.
Form: Oval.
Hilum: Narrow, oval.
Base: Rounded.
Apex: Acuminate.
Sides: Equal.
Tip: 3/16" [4.8 mm.] long with an angle of 40 degrees.
Surface: Irregularly furrowed and ridged toward the apex, pitted toward the base.
Ridges: Jagged.
External color: Deep reddish brown [41. deep rBr].
Pit wall color when cracked: Deep brown [56. deep Br].
Cavity surface color: Strong yellowish brown [74. s.yBr].
Average pit wall thickness: 7/32" [5.6 mm.].
Average width: 7/8" [22.2 mm.].
Average length: 1 1/4" [31.8 mm.].
Average breadth: 5/8" [15.9 mm.].
Tendency to split: None observed.
Kernel:
*Form*.—Oval.
*Skin color*.—Moderate orange yellow [71. m.OY].
*Pellicle color*.—Grayish brown [61. gy.Br].
*Vein color*.—Moderate brown [58. m.Br].
*Taste*.—Bitter.
*Viable*.—Yes.
*Average width*.—7/16" [11.1 mm.].
*Average length*.—11/16" [17.5 mm.].
*Amygdalin*.—Abundant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Majestic Pearl' (U.S. Plant Pat. No. 18,778) nectarine by being a vigorous tree, by being self-fertile, and by producing nectarines that are clingstone in type, globose in shape, full red in skin color, genetically white in flesh color, and firm in texture, but is distinguished therefrom by blooming earlier, by requiring less chilling hours, by having globose instead of reniform leaf glands, and by producing fruit that is somewhat sweeter and slightly more acidic in flavor, and that matures eight days later.

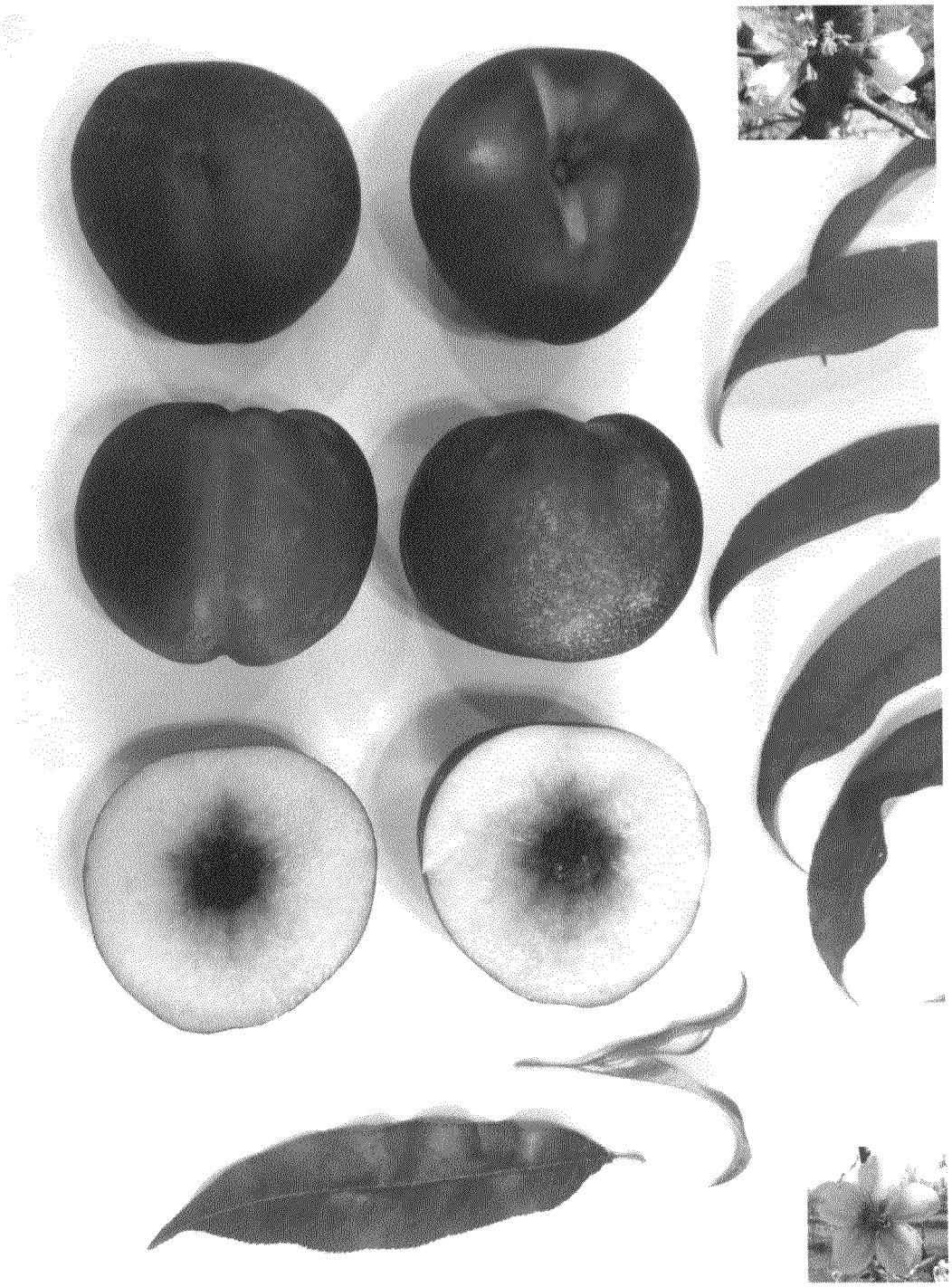

* * * * *